(12) United States Patent
van der Weide

(10) Patent No.: US 7,179,587 B2
(45) Date of Patent: Feb. 20, 2007

(54) METHOD AND APPARATUS FOR HIGH FREQUENCY INTERFACING TO BIOCHEMICAL MEMBRANES

(75) Inventor: Daniel W. van der Weide, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 751 days.

(21) Appl. No.: 10/306,849

(22) Filed: Nov. 27, 2002

(65) Prior Publication Data

US 2003/0129737 A1 Jul. 10, 2003

Related U.S. Application Data

(60) Provisional application No. 60/334,378, filed on Nov. 30, 2001.

(51) Int. Cl.
*C12N 13/00* (2006.01)
*C12M 1/42* (2006.01)
(52) U.S. Cl. ............ 435/4; 435/173.4; 435/287.1
(58) Field of Classification Search ............ 435/4, 435/29, 287.1, 173.4
See application file for complete search history.

(56) References Cited

U.S. PATENT DOCUMENTS

| | | | |
|---|---|---|---|
| 5,581,349 A | 12/1996 | Halaka | |
| 5,846,708 A | 12/1998 | Hollis et al. | |
| 5,858,666 A | 1/1999 | Weiss | |
| 5,936,237 A | 8/1999 | van der Weide | |
| 6,246,898 B1 | 6/2001 | Vesely et al. | |
| 6,287,776 B1 | 9/2001 | Hefti | |
| 6,287,874 B1 | 9/2001 | Hefti | |
| 2003/0034453 A1 | 2/2003 | Ookubo et al. | |

OTHER PUBLICATIONS

Maria A. Stuchly, et al., "Coaxial Line Reflection Methods for Measuring Dielectric Properties of Biological Substances at Radio and Microwave Frequencies—A Review," IEEE Transactions on Instrumentation and Measurement, vol. IM-29, No. 3, Sep. 1980, pp. 176-183.

D.A. Haydon, et al., "The Admittance of Squid Giant Axon at Radio Frequencies and its Relation to Membrane Structure," J. Physiol., vol. 360, 1985, pp. 275-291.

A. Ashkin, et al., "Observation of a Single-Beam Gradient Force Optical Trap for Dielectric Particles," Optics Letters, vol. 11, No. 5, May 1986, pp. 288-290.

Atticus H. Hainsworth, et al., "Effects of Double-Layer Polarization on Ion Transport," Biophys. J., vol. 51, Jan. 1987, pp. 27-36.

A.S. Pasynkov, "Polarizability of Bilayer Membranes on Phase Separation. Quasi-One-Dimensional Model," Biophysics, vol. 32, No. 1, 1987, pp. 54-59.

Karunanayake P.A.P. Esselle, et al., "Capacitive Sensors for In-Vivo Measurements of the Dielectric Properties of Biological Materials," IEEE Transactions on Instrumentation and Measurement, vol. 37, No. 1, Mar. 1988, pp. 101-105.

Thor Osborn, et al., "An Approach to the Stabilization of Lipid Bilayers Incorporating Ion Channels for Biosensing Applications," IEEE Engineering in Medicine & Biology Society 11th Annual International Conference, 1989, pp. 1375-1376.

Satoru Mashimo, et al., "Dielectric Study on Dynamics and Structure of Water Bound to DNA Using a Frequency Range 107-1010 Hz," J. Phys. Chem, vol. 93, 1989, pp. 4963-4967.

John Sandblom, et al., "The Effect of Microwave Radiation on the Stability and Formation of Gramicidin-A Channels in Lipid Bilayers Membranes," Bioelectromagnetics, vol. 12, 1991, pp. 9-20.

Lars Malmqvist, et al., "Trapped Particle Optical Microscopy," Optics Communications, vol. 94, 1992, pp. 19-24.

Yu D. Feldman, et al., "Time Domain Dielectric Spectroscopy. A New Effective Tool for Physical Chemistry Investigation," Colloid & Polymer Science, vol. 270, 1992, pp. 768-780.

G. Fuhr, et al., "Radio-Frequency Microtools for Particle and Live Cell Manipulation," Naturwissenschaften, vol. 81, 1994, pp. 528-535.

James Baker-Jarvis, et al., "Analysis of an Open-Ended Coaxial Probe with Lift-Off for Nondestructive Testing," IEEE Transactions on Instrumentation and Measurement, vol. 43, No. 5, Oct. 1994, pp. 711-718.

Cy Tamanaha, et al., "An Inorganic Filter to Support Biomembrane-Mimetic Structures," 1995 IEEE-EMBC and CMBEC, Theme 7: Instrumentation, 1995, pp. 1559-1569.

S.I. Alekseev, et al., "Millimeter Microwave Effect on Ion Transport Across Lipid Bilayer Membranes," Bioelectromagnetics, vol. 16, 1995, pp. 124-131.

Vitaliy I. Geletyuk, et al., "Dual Effects of Microwaves on Single Ca2+-Activated K+ Channels in Cultured Kidney Cells Vero," FEBS Letters, vol. 359, 1995, pp. 85-88.

Geoff Smith, et al., "Dielectric Relaxation Spectroscopy and Some Applications in the Parmaceutical Sciences," Pharmaceutical Sciences, vol. 84, No. 9, Sep. 1995, pp. 1029-1043.

(Continued)

*Primary Examiner*—James Ketter
(74) *Attorney, Agent, or Firm*—Foley & Lardner LLP

(57) ABSTRACT

High frequency interfacing to biochemical membranes, such as supported bilayers and cell membranes, is carried out by supporting a biochemical membrane on a support surface while allowing access to the surface of the membrane through an opening in the support. A sharp tipped probe is positioned adjacent to the exposed surface of the membrane. The probe may have an inner core tip and a coaxial shield around the core tip that is electrically insulated therefrom. Radio frequency power is supplied to the probe to apply a localized radio frequency field to the membrane adjacent to the probe. Transport and binding events at the membrane are detected by changes in the field transmitted through the membrane and received by a receiving probe, or reflected from the membrane and received by the transmitting probe, and coupled therefrom to a detector for detection.

23 Claims, 13 Drawing Sheets

OTHER PUBLICATIONS

Andreas Janshoff, et al., "Applications of Impedance Spectrocscopy in Biochemistry and Biophysics," Acta Biochimica Polonica, vol. 43, No. 2, 1996, pp. 339-348.

D.W. van der Weide, et al., "The Nanoscilloscope: Combined Topography and AC Field Probing with a Micromachined Tip," J. Vac. Sci. Technol. B., vol. 14, No. 6, Nov./Dec., 1996, pp. 4144-4147.

D.W. van der Weide, "Localized Picosecond Resolution with a Near-Field Microwave/Scanning-Force Microscope," Applied Physics Letters, vol. 70, No. 6, Feb. 10, 1997, pp. 677-6797.

Lukas Novotny, et al., "Theory of Nanometric Optical Tweezers," Physical Review Letters, vol. 79, No. 4, Jul. 28, 1997, pp. 645-648.

Juris Galvanovskis, et al., "Amplification of Electromagnetic Signals by Ion Channels," Biophysical Journal, vol. 73, Dec. 1997, pp. 3056-3065.

Charles L. Asbury, et al., "Trapping of DNA in Nonuniform Oscillating Electric Fields," Biophysical Journal vol. 74, Feb. 1998, pp. 1024-1030.

D.A. Simson, et al., "Mircopipet-Basd Pico Force Transducer: In Depth Analysis and Experimental Verification," Biophysical Journal, vol. 74, Apr. 1998, pp. 2080-2088.

Michael P. Hughes, et al., "Manipulation of Herpex Simplex Virus Type I by Dielectrophoresis," Biochimica et Biophysica Acta, vol. 1425, 1998, pp. 119-126.

Web pages entitled "CMBE Interdisciplinary Research Expertise in the Technology of Functional Molecular Layers," printed Jul. 24, 1999.

Web pages entitled "The ICS Biosensor-Functional Overview-AMBRInstitute," pp. 1-8, printed Jul. 30, 1999.

Thierry Stora, et al., "Ion-Channel Gating in Transmembrane Receptor Proteins: Functional Activity in Tethered Lipid Membranes," Angew. Chem. Int. Ed., vol. 38, No. 3, 1999, pp. 389-392.

Christian Schmidt, et al., "A Chip-Based Biosensor for the Functional Analysis of Single ion Channels," Angew. Chem. Int. Ed., vol. 39, No. 17, 2000, pp. 3137-3140.

J.E.M. McGeoch, et al., "Biological-to-Electronic Interface with Pores of ATP Synthase Subunit C in Silicon Nitride Barrier," Med. Biol. Eng. Comput., vol. 38, 200, pp. 113-119.

Wolfgang Meier, et al., "Reconstitution of Channel Proteins in (Polymerized) ABA Triblock Copolymer Membranes,"Angew. Chem. Int. Ed., vol. 39, No. 24, 2000, pp. 4599-4602.

G.I. Ovchinnikova, "The Role of Charge Transport in the Reception of Electromagnetic Radiation,"Critical Reviews in Biomedical Engineering, 2000, pp. 77-82.

Hagan Bayley, et al., "Resistive-Pulse Sensing—From Microbes to Molecules," Chem. Rev., vol. 100, 2000. pp. 2575-2594.

Frida Ryttsen, et al., "Characterization of Single-Cell Electroporation by Using Patch-Clamp and Fluorescence Microscopy," Biophyscial Journal, vol. 79, Oct., 2000, pp. 1993-2001.

Shigeru Amemiya, et al., "Scanning Electrochemical Microscopy. 40. Voltammmetric Ion-Selective Micropipet Electrodes for Probing Ion Transfer at Bilayer Lipid Membranes," Analytical Chemistry, vol. 72, No. 20.

Samual Terrettaz, et al., "Immunosensing by a Synthetic Ligand-Gated Ion Channel," Angew. Chem. Int. Ed, vol. 40, No. 9, 2001, pp. 1740-1743.

Erwin Neher, "Molecular Biology Meets Microelectronics," Nature Biotechnology, vol. 19, Feb. 2001, p. 114.

Israel Garcia-Ruiz, et al., "Measuring Complex Permittivity of Materials for Frequencies Under 18 GHz," Applied Microwave & Wireless, Jun. 2001, pp. 56-66.

A. Maureen Rouhi, "From Membranes to Nanotubules," Chemical & Engineering News, Jun. 11, 2001, pp. 29-33.

Petra Schwille, et al., "Analyzing Single Protein Molecules Using Optical Methods," Current Opinion in Biotechnology, vol. 12, 2001, pp. 382-386.

Serge G. Lemay, et al., "Two-Dimensional Imaging of Electronic Wavefunctions in Carbon Nanotubes," Nature, vol. 412, Aug. 9, 2001, pp. 617-620.

M. Mandel, "The Electric Polarization of Rod-Like, Charged Macromolecules,", 1961, pp. 489-496.

G. Stark, "Rectification Phenomena in Carrier-Mediated Ion Transport," Chimica et Biophysica Acta, vol. 298, 1973, pp. 323-332.

V.V. Tyazhelov, et al., "Change in the Conductivity of Phospholipid Membranes Modified by Alamethicin on Exposure to a High Frequency Electromagnetic Field," Biophysics, vol. 23, 1979, pp. 750-751.

Theo Odijk, "Possible Scaling Relations for Semidilute Polyelectrolyte Solutions," Macromolecules, vol. 12, No. 4, Jul./Aug. 1979, pp. 688-693.

Mark A. Hollis, et al., "A Swept-Frequency Magnitude Method for the Dielectric Characterization of Chemical abd Biological Systems," IEEE Transactions on Microwave Theory and Techniques, vol. MTT-28, No. 7, Jul. 1980, pp. 791-801.

Tip height: ~20 micron
Tip opening: ~200 nm
Cantilever: ~250x90x5 micron

METHOD AND APPARATUS FOR HIGH FREQUENCY INTERFACING TO BIOCHEMICAL MEMBRANES

CROSS-REFERENCE TO RELATED APPLICATION

This application claims the benefit of provisional application No. 60/334,378, filed Nov. 30, 2001, the disclosure of which is incorporated herein by reference.

REFERENCE TO GOVERNMENT RIGHTS

This invention was made with United States Government support awarded by the following agency: ONR N 000 14-99-1-0717. The United States Government has certain rights in this invention.

FIELD OF THE INVENTION

This invention pertains generally to the field of electrophysiology and to devices and methods for measurement of ion transport across biochemical membranes.

BACKGROUND OF THE INVENTION

Biological membranes such as cell membranes are intrinsically impermeable to ions and polar molecules. Essential transport of ions through a membrane is achieved by channel or pump proteins. The detailed structure of these proteins and their mechanisms in directing ion traffic through pores in the membranes are not completely known. Two types of channels have been identified, one operated by membrane depolarization (examples: sodium and potassium channels) called voltage-gated, and a second operated by receptor binding (such as acetylcholine), known as ligand-gated. The flow of ions through the pores in the membranes can be assessed by electrical conductance measurements. The study of single-channel ion flow is important to the basic understanding of membrane permeability. It also has practical applications in health, chemical sensing, and agriculture in that molecules that block membrane traffic, and that may be useful as pesticides or as a human deterrent, can be identified. Single-channel ion flow can be studied on cell membranes directly or by the use of artificial lipid bilayers and pore forming proteins such as alpha hemolysin ($\alpha$-HL) and peptaibol alamethicin.

Currently, conductance measurements across cell membranes are carried out by the conventional patch-clamp amplifier method. In this technique, a cell is drawn against a glass pipette tip (about 1 μm in diameter) so as to form a tight seal. Generally, the seal must be sufficiently tight that the current path around the seal has a very high resistance (e.g., in the giga-ohm range). The electrical current flowing through the membrane that separates solutions in the pipette and outside is then measured by a conventional electrical circuit. This electrical current is influenced by the flow of ions through a single channel and by its states (gate closed or open). While this method allows monitoring of single channels with a time resolution of microseconds, it is labor and skill intensive and is not suitable for high throughput screening. The conventional patch-clamp amplifier operates from DC to a frequency of 10–100 KHz, and is limited by the greater than 1 giga-ohm input impedance required to convert femptoamp channel currents to readable voltages. Because the technique measures very low levels of current flowing across the membrane, the signal being measured is inevitably associated with significant noise. Conductance measurements are also carried out on planar lipid bilayers, also known as black lipid membranes (BLMs). These are artificial membranes suspended in a small (e.g., 0.1 mm) aperture in which proteins are situated. The patch clamp amplifier apparatus is then used to measure current/voltage characteristics of a single protein or several situated in this membrane as a function of time, ligand binding, etc.

SUMMARY OF THE INVENTION

In accordance with the invention, high-frequency interfacing to biochemical membranes, such as cell membranes and lipid bilayers, is carried out utilizing a probe that provides a highly localized radio frequency field for interaction with localized areas of the membrane. Transport and binding events in the membrane are detected by the effect on the electromagnetic power transmitted through or reflected by the membrane to allow measurement of such events. Such events are believed to change the capacitance and conductance across the membrane to change the high frequency reflection or transmission coefficient at or across the membrane where the protein is located. The detected radio frequency signal has relatively low noise as compared to conventional DC current monitoring systems.

The probe can be positioned adjacent to a membrane, such as a cell membrane, without the need for forming a tight seal with the membrane, significantly reducing the time and skill level required to obtain measurements. In addition, application of the localized field provides a rectified component that provides a DC voltage bias across the membrane, avoiding the need for application of a separate voltage bias across the membrane. Membrane transfer events can further be modulated in accordance with the application of the field from the probe to control transport or binding events. Application of the localized field may also be utilized for trapping and positioning of membrane proteins such as porins and ion channels via dielectrophoresis.

Interface apparatus in accordance with the invention includes a preferably coaxial probe having an inner conductive core tip and a coaxial conductive shield electrically insulated from the core tip. A radio frequency power supply is coupled to the probe to provide a radio frequency drive signal thereto, and a support for a biochemical membrane is positioned closely adjacent to the probe such that a localized microwave field is supplied by the probe. The electromagnetic field applied by the probe as transmitted through or reflected from the membrane is affected by the transport or binding events in the membrane within the field from the probe. The transmitted field may be detected by a receiving probe positioned on the side of the membrane opposite that to which the transmitting probe is mounted, with the received signal being transmitted to a detector such as a spectrum analyzer which detects and records changes in the detected signal. Alternatively, the microwave power reflected from the membrane and received by the probe may be coupled to a detector which similarly determines changes in the reflected signal corresponding to transport or binding events in the membrane.

A probe in accordance with the invention may be formed as a single probe which is mounted to interface with a membrane that is supported on a support substrate and that spans an opening in the substrate. Multiple probes may also be mounted in an array adjacent to a membrane supported by support surfaces under individual fluid holding cells in the

DETAILED DESCRIPTION OF THE INVENTION

Figure 1:
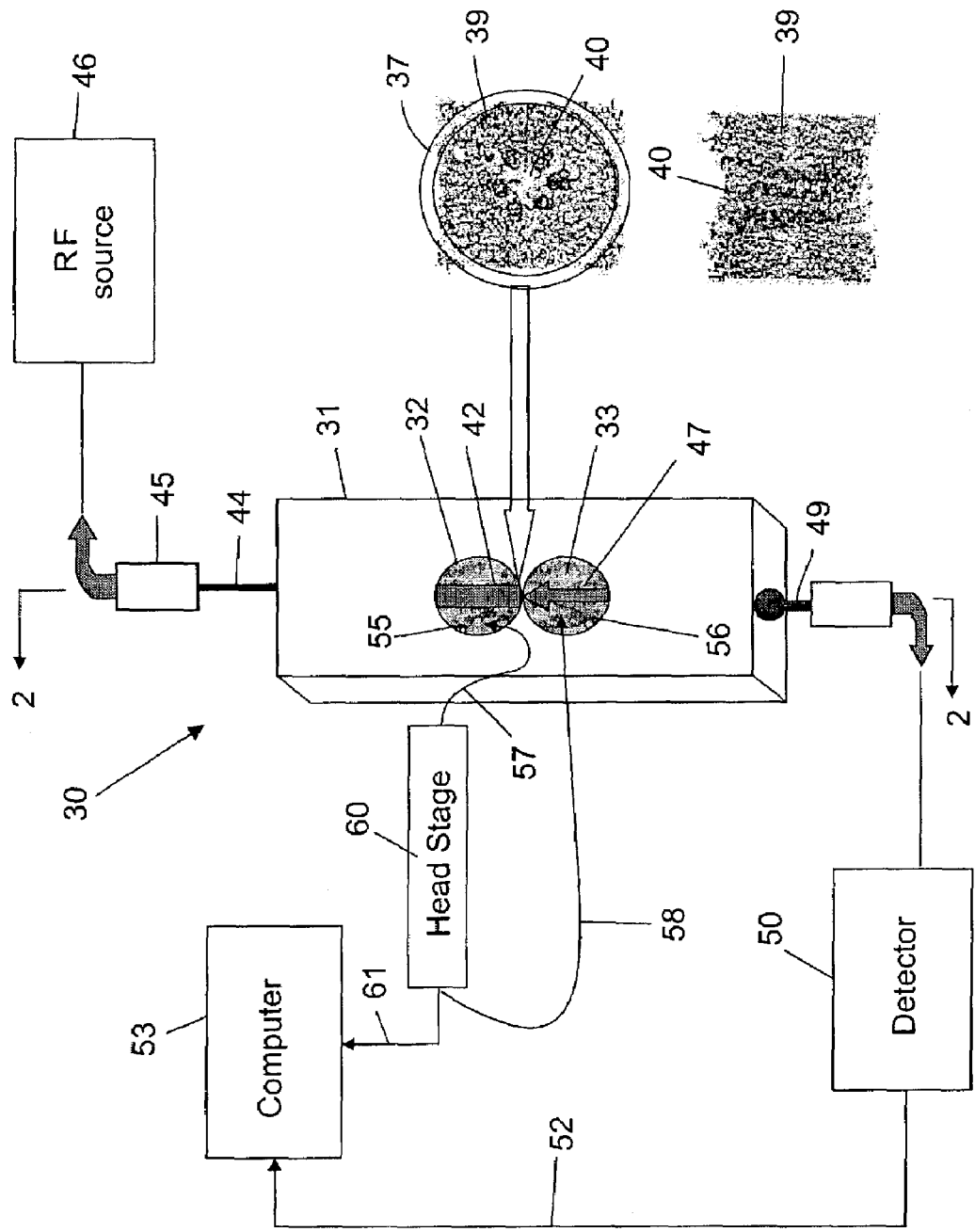
FIG. 1 is a schematic view of apparatus in accordance with the invention for high frequency interfacing with biochemical membranes.
Figure 2:
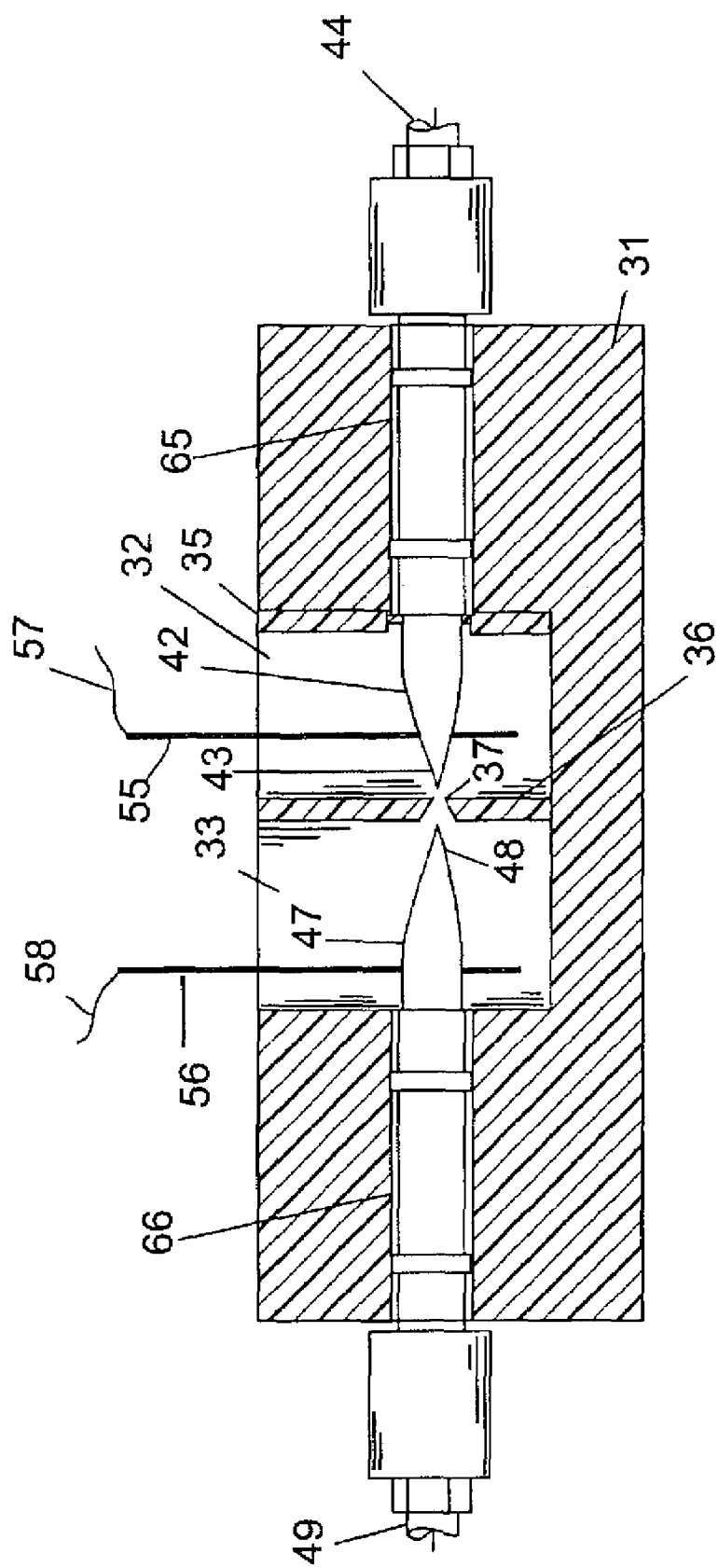
FIG. 2 is a cross-sectional view of a base with containment chambers in which transmitting and receiving probes are mounted in accordance with the invention, taken generally along the lines 2—2 of FIG. 1.

With reference to the drawings, apparatus in accordance with the invention for high frequency interfacing with biochemical membranes is shown generally at 30 in FIG. 1. The apparatus 30 includes a base 31 in which are formed reagent containment chambers 32 and 33. The containment chamber 32 includes a cylindrical shell insert 35 which is inserted into an opening in the base 31 and has an inner wall 36 which forms a support wall for supporting a biochemical membrane that spans and covers an opening 37 (best shown in FIGS. 2 and 3) in the cylindrical walled insert 35. As illustrated schematically in FIG. 1, the opening 37 is of a size (e.g., in the range of 200 μm diameter) selected to allow support of a bilayer membrane, illustrated at 39, which has a protein channel 40 therein through which ion transport can take place. A radio frequency (RF) probe 42 is inserted through the base block 31 to a position wherein the probe tip 43 is closely adjacent to the opening 37, as illustrated in FIG. 2. The transmitting probe 42 is connected via a coaxial cable 44, preferably through a DC blocking element 45 as shown in FIG. 1, to an RF source 46. The RF power supply 46 is preferably capable of providing RF power at selected frequencies, e.g., in the range of tens of MHz to several GHz, e.g., 10 GHz or higher. An example is a Hewlett Packard HP 83650A synthesized sweeper. For purposes of measuring the RF field transmitted across the membrane 39, a receiving probe 47 is mounted in the base 31 extending into the chamber 33 with a probe tip 48 positioned closely adjacent to the opening 37 in a position across the membrane 39 opposite to the tip 43 of the probe 42. The receiving probe 47 is coupled by a coaxial cable 49 to a detector 50, e.g., a spectrum analyzer such as a Hewlett Packard HP 8565E spectrum analyzer. As ions are transported through the channel 40 across the membrane 39, the RF power coupled across the membrane 39 from the probe 42 to the probe 47 will be affected, providing a signal picked up by the receiving probe 47 and detected by the detector 50 which will allow an indication of the frequency and duration of transport or binding events. The output of the detector 50 may be coupled by a connecting line 52 to a computer 53 which is programmed to record the detected events and statistically analyze the accumulated data. In accordance with the present invention, the RF field from the transmitting probe 42 provides a component that is effectively rectified to yield a DC potential across the membrane 39 which induces ion flow without requiring the application of a separate DC voltage across the membrane.

To allow correlation between the data determined in accordance with the invention utilizing the apparatus 30, conventional electrodes 55 and 56 (e.g., Ag—AgCl electrodes) may be mounted in the containers 32 and 33, respectively, and connected via lines 57 and 58 to a head stage 60 including a conventional patch-clamp amplifier. The output data from the patch-clamp amplifier is provided on a line 61 to the computer 53 to allow analysis of the data obtained from the patch-clamp amplifier, which can be correlated with the data obtained from high frequency transmission across the membrane. The head stage 60 may, in a conventional manner, apply a DC voltage between the electrodes 55 and 56 to provide a potential difference across the membrane 39, allowing current flow due to transport events across the membrane 39 which will be detected by the patch-clamp amplifier and submitted as data to the computer 53.

Figure 3:
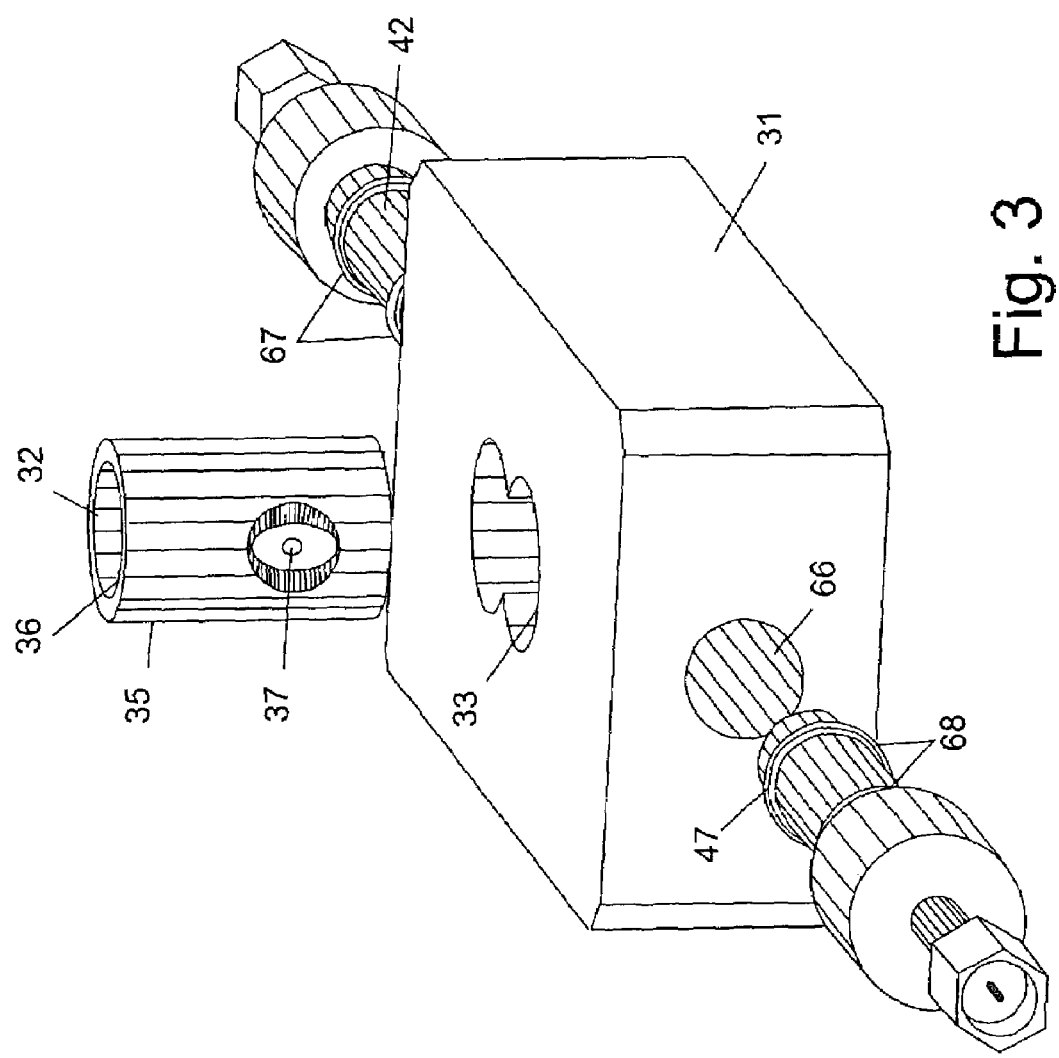
FIG. 3 is a perspective view of the base, transmitting and receiving probes, and a containment chamber insert in position to be mounted within the base.

The base block 31 and the insert 35 that provides the support for the membrane may be formed of conventional bio-compatible material such as Delrin™ acetal plastic. As illustrated in FIG. 3, the transmitting probe 42 and receiving probe 47 may be formed to be inserted in openings 65 and 66 in the base block 31, with fluid tight seals being established by O-rings 67 and 68 on the probes 42 and 47. The removable insert cylinder 35 is conveniently removed from the base block to allow cleaning and application of a new supported bilayer membrane over the interior surface 36 of the cylindrical insert 35, covering the opening 37, after which the cylindrical walled insert 35 may be inserted back in place into the base block 31.

Figure 4:
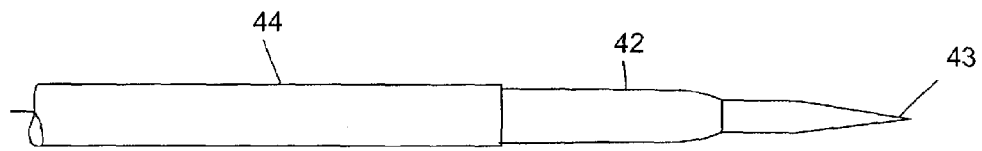
FIG. 4 is a view of a coaxial probe that may be utilized in the apparatus of FIGS. 1–3.
Figure 6:
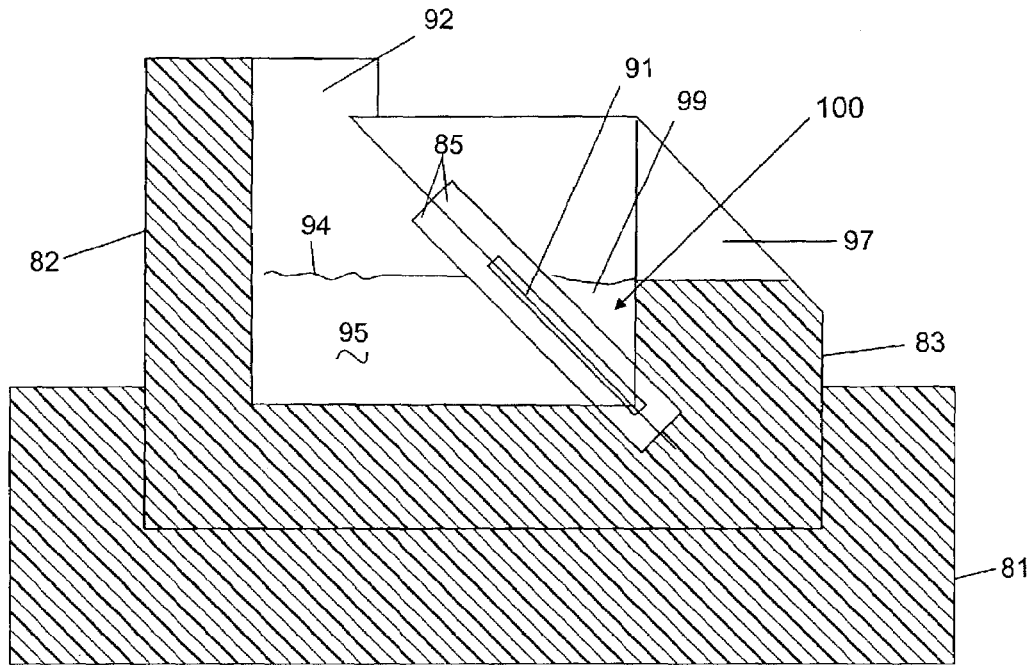
FIG. 6 is a cross-sectional view of the fixture of FIG. 5 taken generally along the lines 6—6 of FIG. 5.
Figure 5:
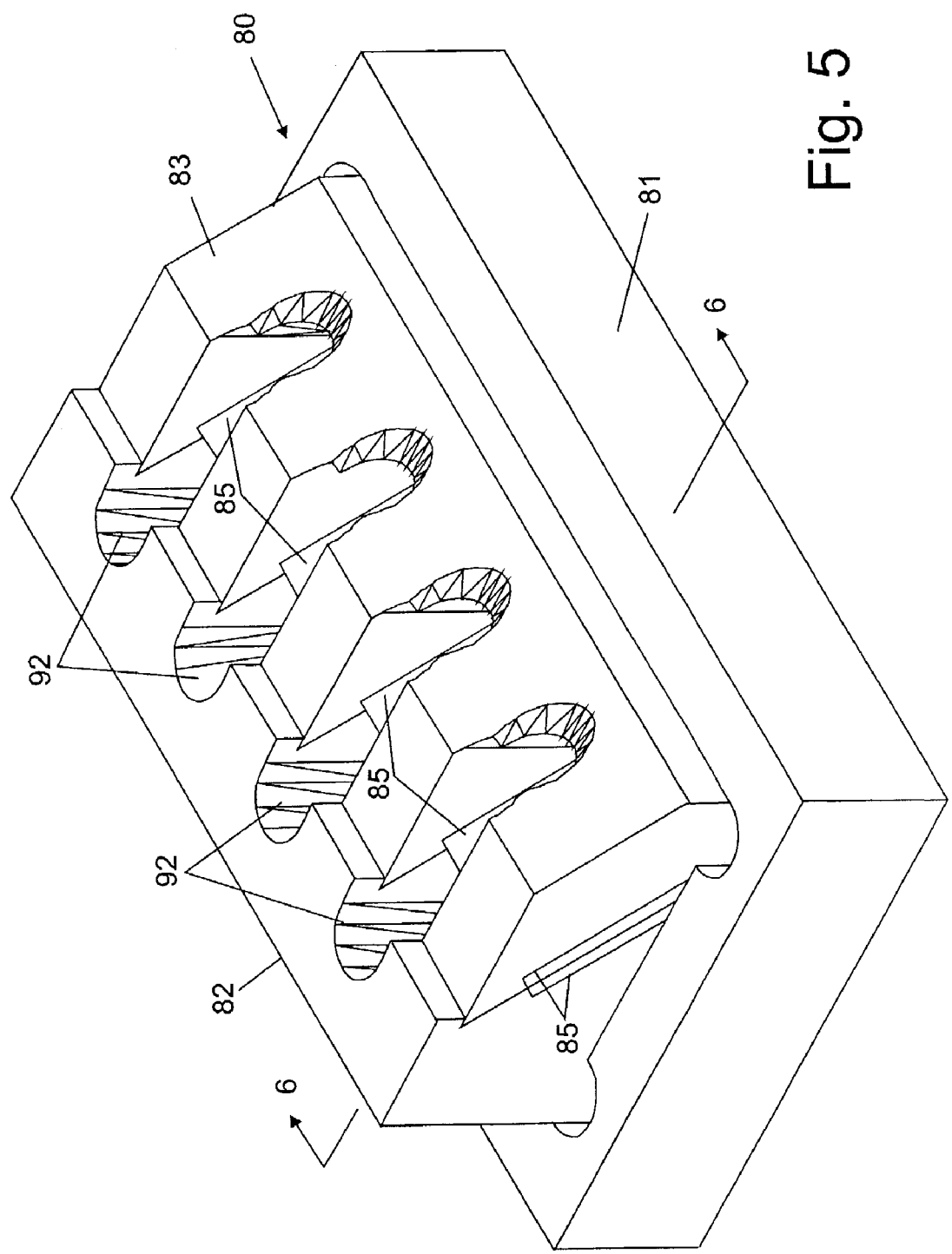
FIG. 5 is a perspective view of a fixture for holding multiple samples in position to be examined sequentially or concurrently utilizing probes in accordance with the invention.

As shown in FIG. 4, the transmitting probe 42 may be formed with a sharp tip 43 which preferably includes an inner conductive core tip and an outer concentric shield conductor that is insulated from the core tip. Appropriate structures may be formed by, for example, drawing a glass pipette down to a sharp point (e.g., ≈1 μm diameter) and coating the outer surface of the glass pipette with a conducting metal to form the core tip, with epoxy and then a conducting metal being applied thereover to form an outer shield conductor electrically insulated from the inner core tip conductor. If desired, a similar coaxial probe structure may be utilized for the receiving probe 47, and other receiving probe structures may also be used.

As an example of the invention using the apparatus 30, both chambers 32 and 33 were filled with an electrolyte consisting of 1 M KCl, 10 mM HEPES, pH 7.3. A solvent-free planar lipid bilayer of 1,2 diphytanoyl-sn-glycero-phosphocholine was painted onto the inner surface 36 of the insert 35, covering the opening 37. Alamethicin was added to the containment chamber 32 to a final concentration of 0.5 μg/ml. A voltage difference of 40 mV was applied across the membrane 39 between the chambers 32 and 33 by the electrodes 55 and 56. Transmembrane currents were recorded with a patch-clamp amplifier (Axopatch 200 B, Axon Instruments). Alamethicin channels normally appear as stochastic "current bursts" with conducting states of 20 to 60 pA. When a 200–500 MHz, 10 mW signal was applied to the transmitting probe 42, a large increase in conduction up to 400 pA was observed. This effect was reversible, as the channel conductance returned to its normal level when the RF field is removed. This result demonstrates local, reversible and contactless control over protein conformation in membranes.

Figure 21:
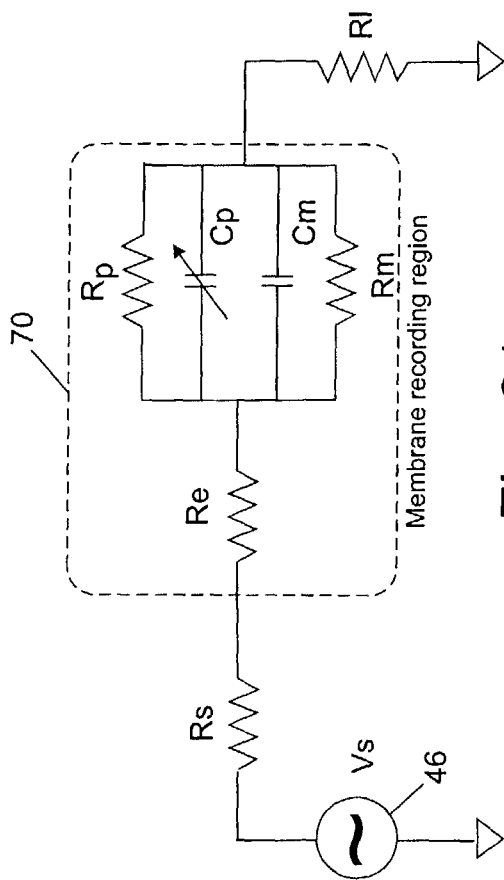
FIG. 21 is an equivalent circuit model for the high frequency interface to the membrane, pore and buffer.

The apparatus 30 was also utilized to modulate alpha-hemolysin pore current and α-hemolysin/β-cyclodextrin with the applied RF, in addition to modulation of alamethicin with applied RF, at various frequencies above 200 MHz including 800–825 MHz. Simultaneous single-porin recordings were made using both the conventional patch-clamp amplifier and the apparatus 30 in transmission mode on native α-hemolysin (α-HL) with β-cyclodextrin (β-CD) flowing through the pore. The high-frequency recordings of the detected RF signal are consistent with a series-capacitor equivalent circuit model of the pore/membrane/buffer interface, with the change in capacitance due to the binding of β-cyclodextrin (ΔC=0.1 fF, a significant change) that is readily measured with high-frequency instrumentation. A circuit model of the interface is shown in FIG. 21, wherein the equivalent circuit elements in the membrane recording region are shown within the dashed line labeled 70. A capacitive increase is found to result in an insertion loss decrease.

Figure 7:
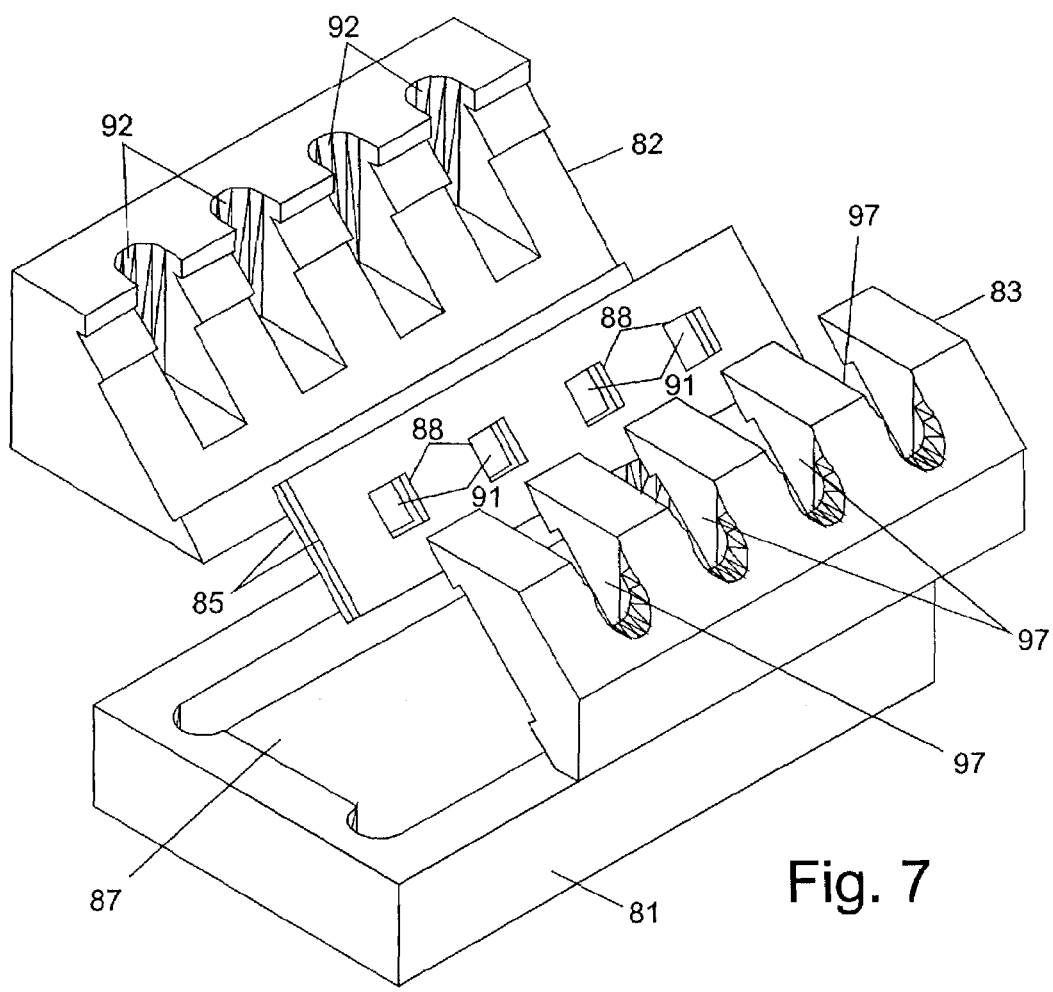
FIG. 7 is an exploded perspective view of the fixture of FIG. 5 showing the parts thereof in position for assembly.
Figure 8:
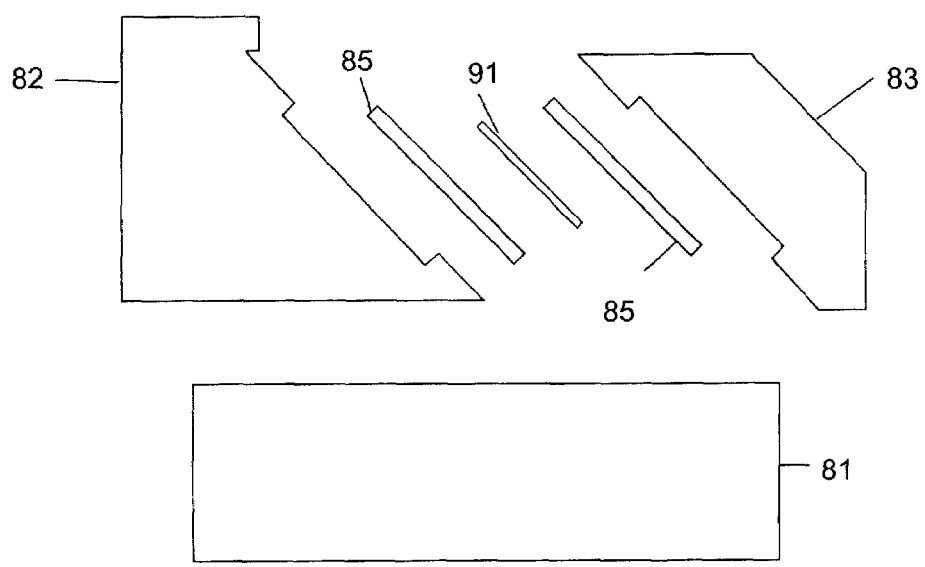
FIG. 8 is an exploded side view of the fixture of FIG. 5 showing the arrangement of parts thereof in position for assembly.

The probe 42 may also be utilized in a reflection mode in which the probe functions both as a transmitting probe and as a receiving probe, with the received RF signal due to reflection from the adjacent membrane being coupled out of the coaxial cable 44 to a detector such as the detector 50 of FIG. 1. FIGS. 5–8 illustrate the construction of a fixture 80 that may be utilized for carrying out multiple simultaneous or sequential reflection mode procedures on multiple membranes. The fixture 80 includes a base 81 in which are mounted a reservoir block 82 and a front clamp block 83. As illustrated in FIGS. 7 and 8, the reservoir block 82 and front clamp block 83 are formed to engage and hold gasket plates 85 and, when they are engaged tightly together over the gasket plates 85, they fit into a depression 87 formed in the base block 81. The gasket plates 85 have window openings 88 formed therein, and are formed to mount support substrate plates 91 between them to expose the surfaces of the support plates 91 at the windows 88. The support plates 91 are formed as flat thin plates of a non-reactive material (e.g., silicon nitride) which have a small opening formed therein (not shown) over which can be formed a bilayer membrane as discussed above. The reservoir block 82 has several spaced containment reservoirs 92 formed therein which are partially covered by the gaskets 85 and the support substrates 91 when the front clamp block 83 and the reservoir block 82 are engaged together and inserted into the base block 81, as illustrated in the cross-sectional view of FIG. 6, forming an enclosed reservoir volume 94 in which a liquid 95 may be contained so that the liquid 95 is in contact with the support substrate 91. The clamp-block 83 has corresponding cutouts 97 formed therein which permit access to the support substrates 91 by a coaxial probe such as the probe 42 discussed above. The front clamp block 83 also has indentations 99 formed therein below the level of the cutouts 97 which, with the gaskets 85 and the support substrate 91, defines an enclosed region which can hold a liquid 100 that will be in contact with the side of the support substrate 91 opposite to the side which is in contact with the liquid 95. Thus, transport can take place across a membrane supported by the support substrate 91 through the opening (or openings) in the substrate 91 between the liquid 95 on one side of the support substrate and the liquid 100 on the other side of the support substrate. Such events will be detected by the probe 42, operating in the reflection mode.

The base 81, reservoir block 82 and clamp block 83 may be formed of conventional bio-compatible materials, such as Delrin™ plastic. The gaskets 85 are conveniently formed of various elastic polymers, for example, polydimethylsiloxane (PDMS).

Figure 9:
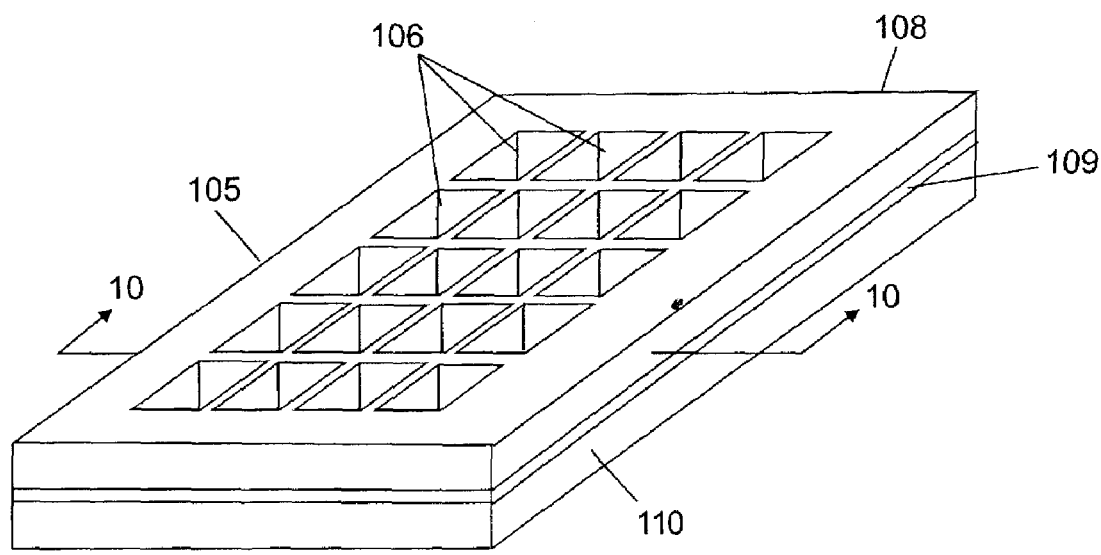
FIG. 9 is a perspective view of apparatus in accordance with the invention which has multiple fluid holding cells in a test fixture for testing multiple samples simultaneously.
Figure 10:
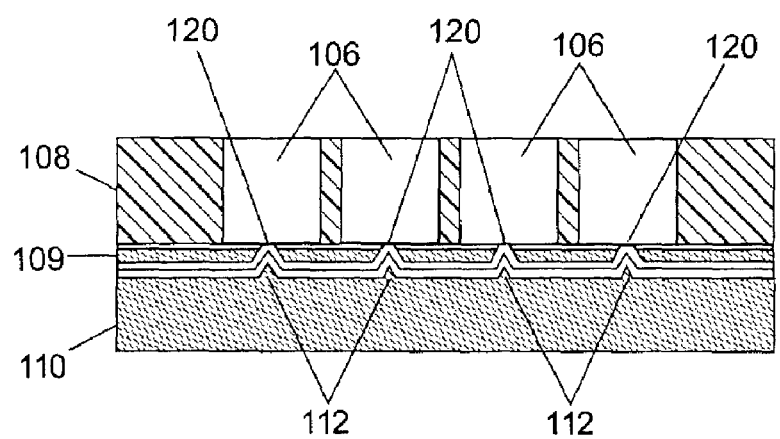
FIG. 10 is a cross-sectional view through the apparatus of FIG. 9 taken generally along the lines 10—10 of FIG. 9.
Figure 11:
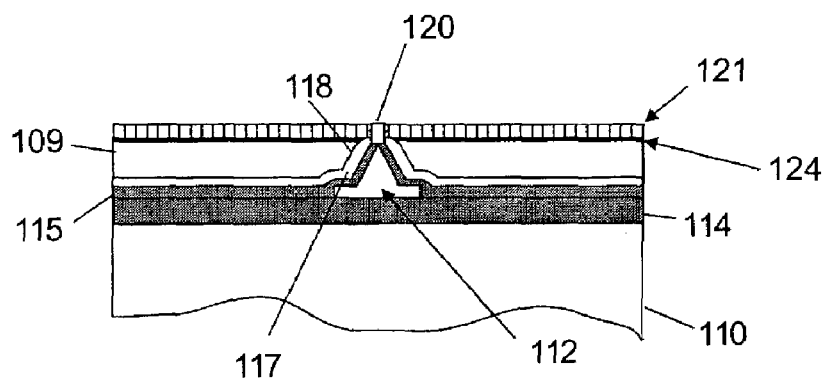
FIG. 11 is a more detailed view of the coaxial probe tip positioned adjacent to a supported membrane that may be utilized in the apparatus of FIGS. 9 and 10.
Figure 12:
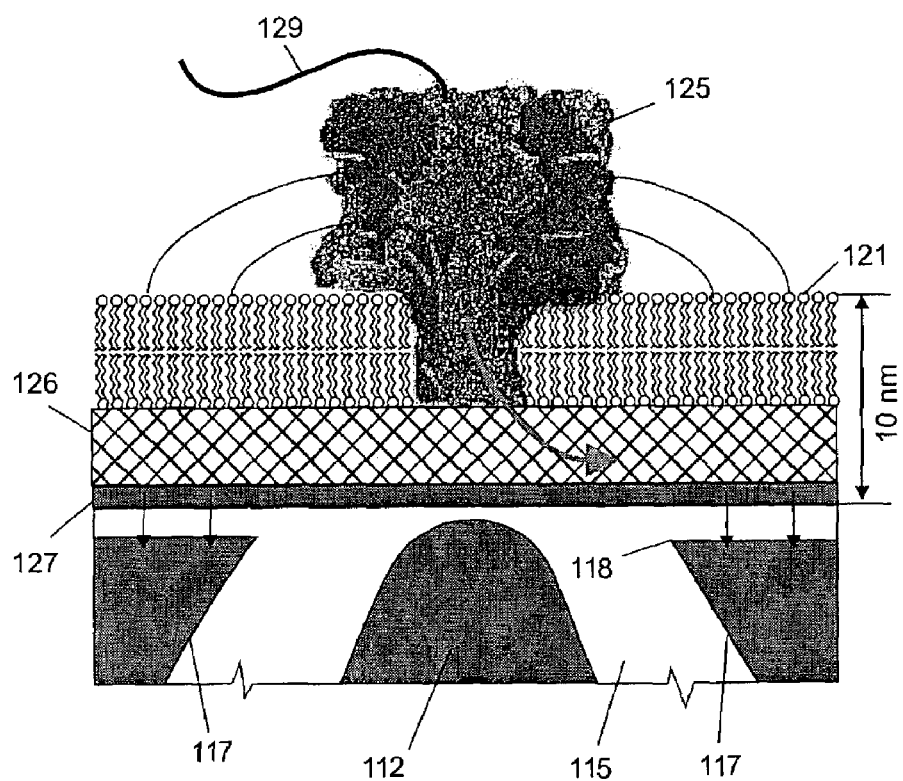
FIG. 12 is an illustrative view showing a core protein formed in a lipid bilayer supported above a probe in accordance with the invention.

For the screening of multiple analyte samples, it is desirable to be able to carry out multiple tests simultaneously. The present invention may be embodied in parallel processing arrangements in which an array of test cells are concurrently and individually tested and monitored. An example of such a test fixture is shown generally at 105 in FIG. 9. The test fixture 105 has multiple fluid holding cells 106 arranged in a two-dimensional rectangular array formed in a face plate 108. Beneath the face plate 108 is a membrane support substrate 109 and a base 110. The probe base 110 has multiple probes with probe core tips 112 formed therein, one of which underlies each of the cells 106, as shown in the cross-sectional view of FIG. 10 and in more detail in the view of FIG. 11. As illustrated in FIG. 11, the core tips 112 may be formed by micromachining techniques of a conducting material, such as doped silicon, that is deposited on a conducting layer or strip 114 and covered with an insulating layer, e.g., silicon dioxide, or a spacer layer. Ionic solution is provided to the supported membrane in a region 115 around the core tip 112, as illustrated in FIG. 12. The outer shield conductor of the coaxial tip may be formed as a layer 117 on the inner surface of an opening 118 formed in the support substrate 109 (e.g., glass or other insulating material). The opening 118 may taper down to a small aperture 120, with a bilayer membrane 121 extending over the aperture 120 and over a support surface 124 (e.g., a gold coated surface for support of the bilayer membrane 121). FIG. 12 illustrates an engineered core protein 125 formed in the lipid bilayer 121, above the probe tip 112, and supported on a hydrophilic support layer 126 and an adhesion monolayer 127. An analyte pathway 129 extends through the pore protein 125 and through the hydrophlic support layer 126.

The multiple probes in the array may be incorporated into feedback loops with individual oscillators, or the probes in the array may be supplied from a single oscillator power source through a multiplexer switch.

Figure 13:
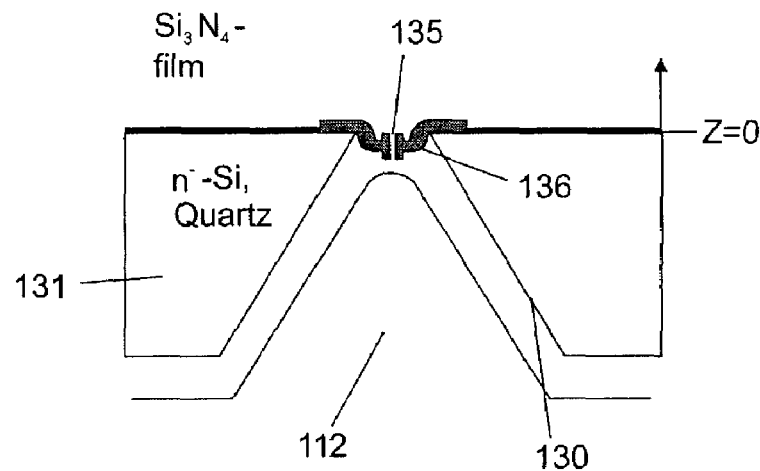
FIG. 13 is a further view of an example of a bilayer membrane supported above a probe in accordance with the invention.

A further example of such an array structure is shown in FIG. 13, in which the core tip 112, covered by an insulating layer such as silicon dioxide, is mounted in an opening 130 in a support substrate 131 such as n-type silicon or quartz, with an insulating film 133 (e.g., $Si_3N_4$) formed on the surface of the support substrate 131. A membrane 135, such as a cell membrane, spans the narrow aperture 136 at the top of the opening 130, with the terminus of the probe tip 112 mounted closely adjacent to the cell membrane 135.

Figure 14:
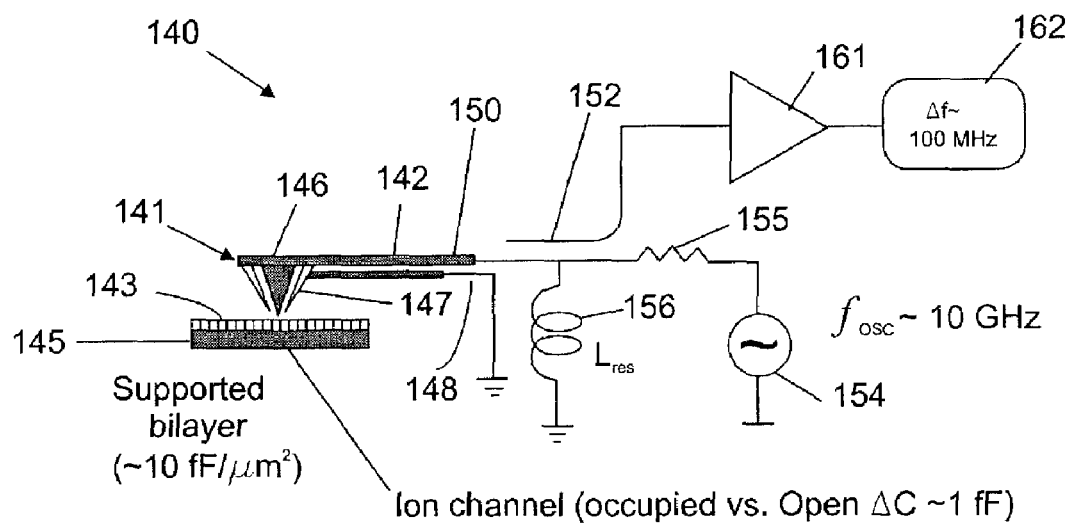
FIG. 14 is a schematic view of a scanning coaxial probe system that may be utilized to scan a supported membrane in accordance with the invention.
Figure 15:
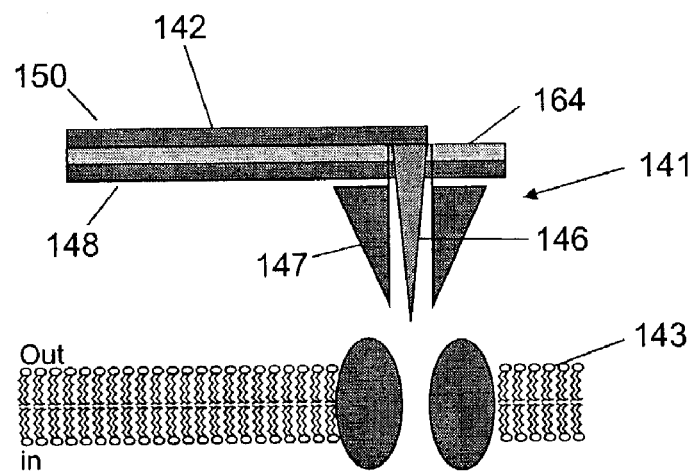
FIG. 15 is a more detailed view showing positioning of a scanning coaxial probe adjacent to a supported membrane, showing a calcium channel for purposes of illustration.

The present invention may also be incorporated in a scanning probe which is displaced relative to a membrane. A scanning probe apparatus in accordance with the present invention is shown generally at 140 in FIG. 14. The apparatus 140 includes a coaxial probe 141 at the end of a cantilever beam 142 positioned over a membrane 143 supported on a support substrate 145. The probe 141 includes an inner core tip 146 and an outer coaxial conducting shield 147. The outer coaxial shield 147 may be connected by a conductor 148 to ground, and the inner core tip 146 may be connected by a line 150 to a directional coupler 152. The directional coupler 152 receives power from a power supply 154 through a coupling resistance 155 and an inductance to ground 156, and directs the power on the conducting line 150 to the core tip 141 which provides a localized electromagnetic field to the adjacent supported bilayer membrane 143. The reflected RF signal received by the probe is passed back to the directional coupler 152 which directs it on a conducting line 160 to an amplifier 161 and a detector 162. An occupied versus an open ion channel will be manifested as a change in the capacitance as coupled to the probe tip 146, which changes the frequency of the RF signal passed back by the directional coupler 152 to the detector 161. Such changes in frequency can be easily and accurately detected, providing a highly sensitive and relatively noise immune process to locate ion channels in the membrane 143 and to detect ion channel transport events. The positioning of the coaxial probe 141 adjacent to a calcium channel in the bilayer 143, is illustrated in FIG. 15. As shown therein, the conductors 148 for the outer shield conductor 147 and the conductor 150 for the inner core tip 146 may be electrically insulated from one another on the beam 142 by an insulating layer 164.

Figure 16:
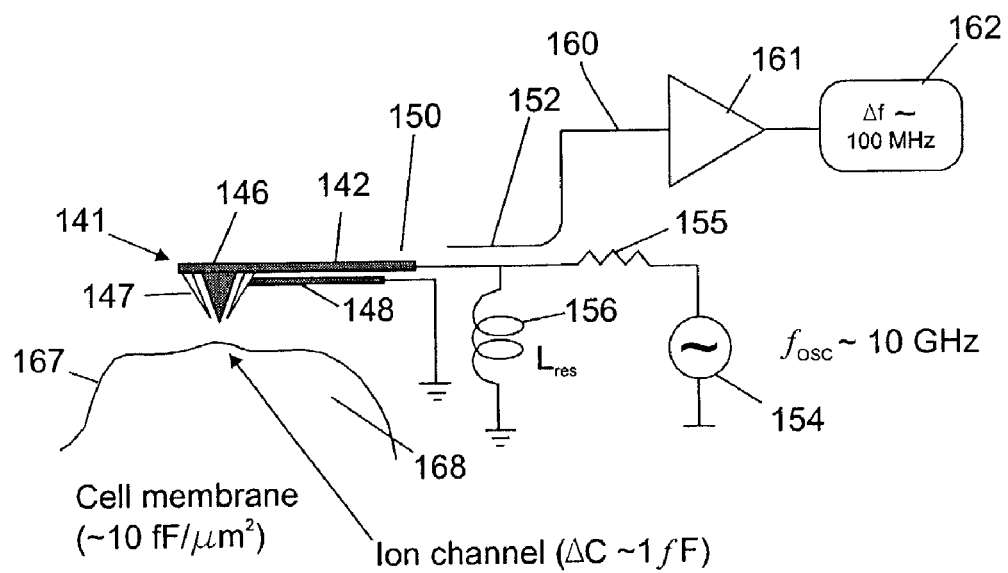
FIG. 16 is a schematic view of a scanning probe in accordance with the invention shown in position to scan over a cell membrane.

As illustrated in FIG. 16, the biochemical membrane may be the outer cell membrane 167 of a biological cell 168. The probe 141 may be scanned over the surface of the cell 168 to search for and detect the channels in the cell membrane and to monitor channel activity, as well as providing an image of the cell.

Figure 18:
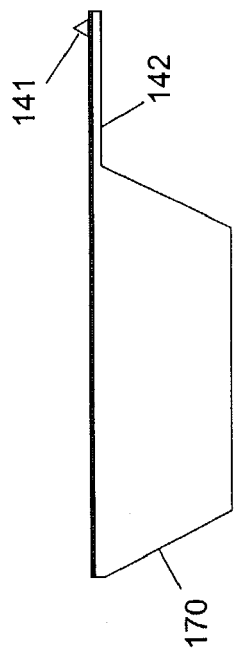
FIG. 18 is a side view of a supported scanning probe tip of the type shown in FIG. 17.
Figure 17:
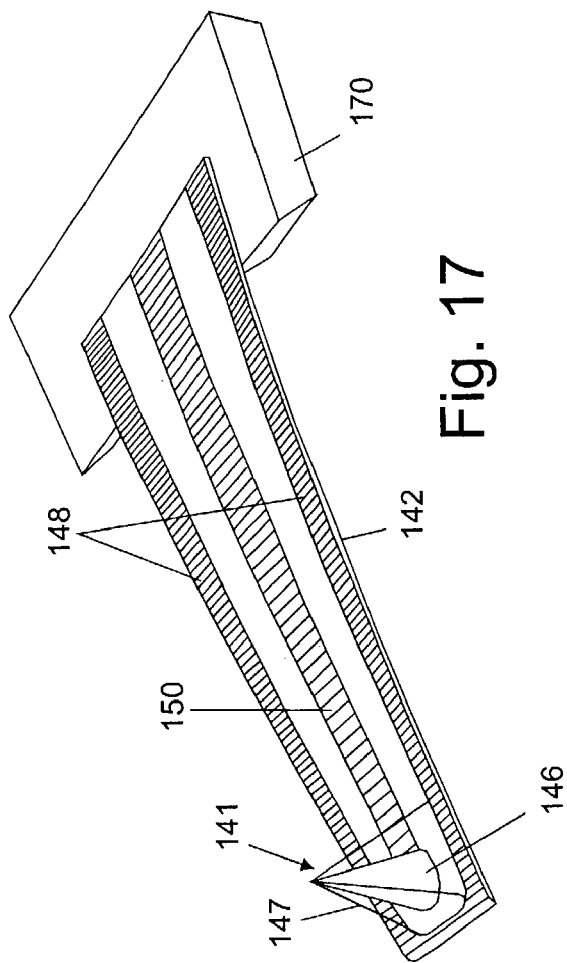
FIG. 17 is a perspective view of a supported scanning probe that may be utilized in the scanning systems of FIGS. 14 and 16.
Figure 19:
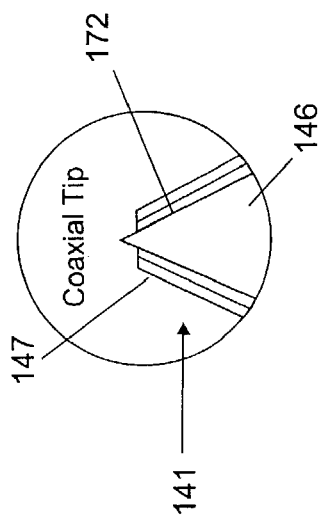
FIG. 19 is a more detailed view of the coaxial probe tip of the scanning probe structure shown in FIGS. 17 and 18.

An exemplary structure for formation of the probe is shown in FIGS. 17 and 18, in which the cantilever 142 is formed by micromachining of a base 170 of, e.g., silicon, with the conductors 148 and 150 formed as conducting metal plated onto the cantilever beam section 142 (as illustrated in FIG. 17). As illustrated in FIG. 19, the coaxial tip may be formed of a center pyramidal silicon core structure 146, a surrounding insulating layer 172 of silicon dioxide, and an outer coaxial conductor 147 of a conducting metal such as aluminum. Micromachining techniques for forming coaxial tips of this type are known to those of ordinary skill in the art. Suitable cantilever beam supported coaxial probe tips are described in U.S. Pat. No. 5,936,237 to van der Weide, the disclosure of which is incorporated herein by reference.

Figure 22:
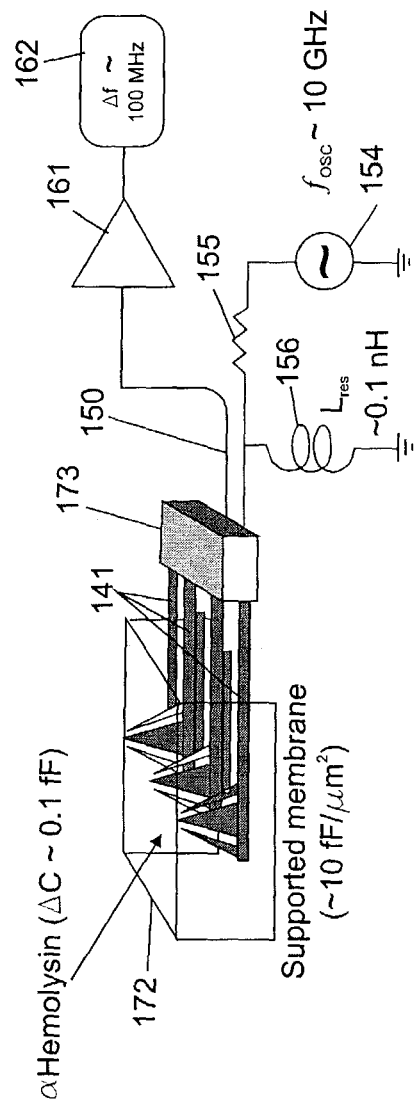
FIG. 22 is a schematic view of a multiple probe array.

Multiple probes of the type described above may be mounted to provide multiple readings on a supported membrane. FIG. 22 illustrates multiple probes 141 mounted beneath a supported membrane 172 (e.g., α-hemolysin), with the probes 141 coupled to the power supply 154 and detector 162 via a multiplexer 173. Alternatively, each probe 141 could have its own oscillator power supply. Analyte flow may be provided by diffusion or pumping.

Figure 20:
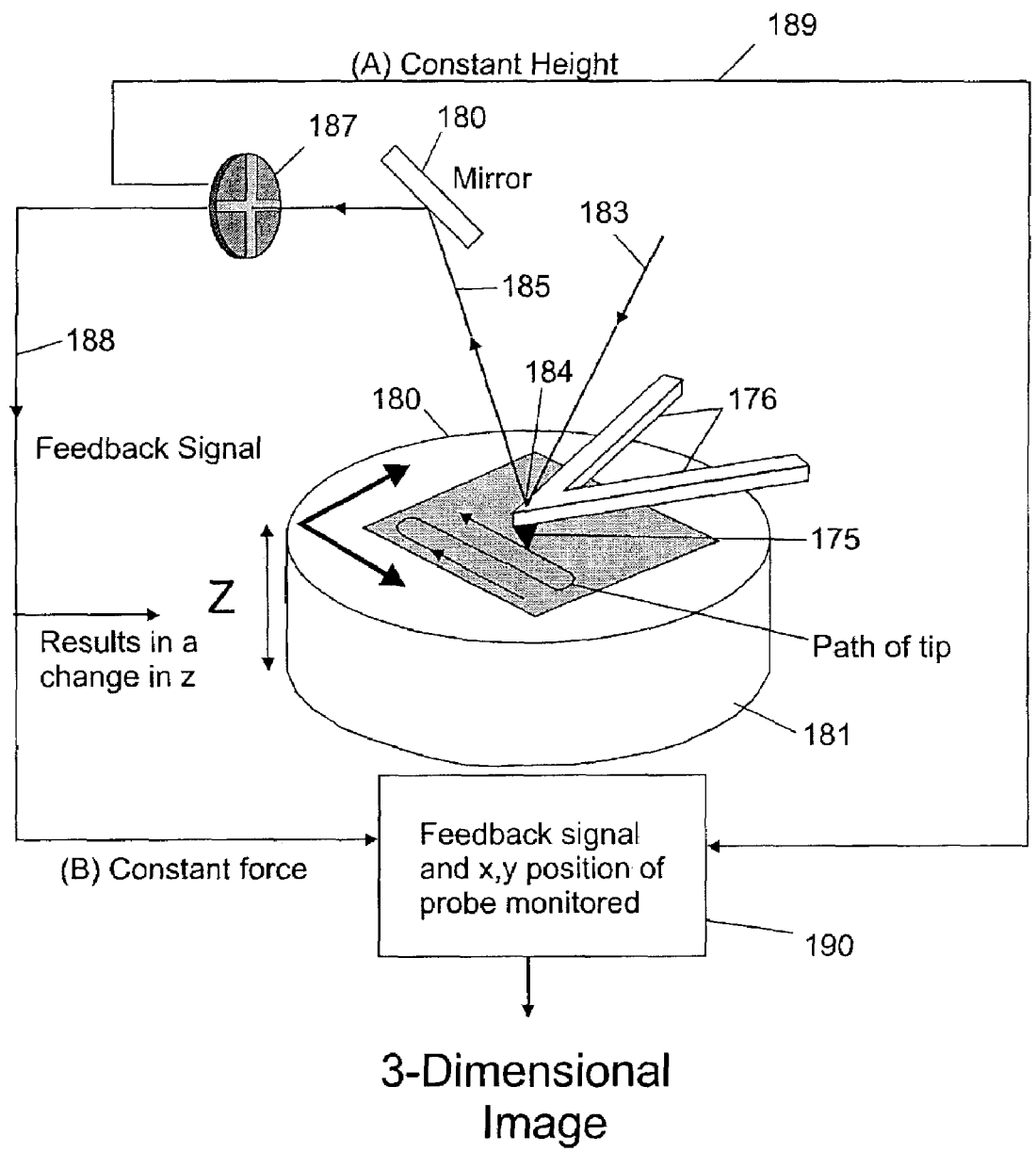
FIG. 20 is a simplified view of a scanning system for supporting a coaxial probe in accordance with the invention for relative movement with respect to a supported membrane.

The cantilever mounted coaxial probe 141 may be mounted for scanning movement over a sample utilizing, for example, conventional scanning force microscope mounting structures, an example of which is illustrated in FIG. 20. In this case, the probe comprising the mount base 170, cantilever beam 142 and probe tip 141 are mounted at an end 175 of a cantilever beam holder 176. The sample 180 to be probed is mounted on piezoscanner bed 181 which is capable of displacement in two dimensions. A laser beam 183 is directed to reflect off an end face 184 of the cantilever to form a reflected beam 185 that is deflected by a mirror 186 to a photodetector 187. The detector 187 provides a feedback signal on a line 188 for force and on a line 189 for height to a processor 190 which processes the information to provide a scanning signal indicating the height and position of the cantilever mounted probe. In the present invention, the probe may be mounted for constant height and the sample 180 be moved relative to the cantilever, or the cantilever supported probe moved relative to the sample, in a two-dimensional pattern (e.g., a conventional raster pattern) to scan over the surface of the supported membrane and locate transport channels in the membrane. The probe can, if desired, be positioned over a channel to allow monitoring of the particular channel. As indicated above, the probe may also be used in the configuration of FIG. 16 as a scanning force microscope probe to scan over the surface of an irregularly shaped object, such as a cell, to provide a scanning force microscope image of the cell and to locate transport channels in the cell membrane.

It is understood that the invention is not confined to the particular embodiments set forth herein as illustrative, but embraces all such forms thereof as come within the scope of the following claims.

What is claimed is:

1. Apparatus for high frequency interfacing to biochemical membranes comprising:
   (a) a coaxial probe having an inner conductive core tip and a coaxial conductive shield electrically insulated from the core tip;

(b) a radio frequency power supply coupled to the coaxial probe to provide a radio frequency drive signal thereto; and (c) a support for a biochemical membrane positioned closely adjacent to the coaxial probe such that a localized microwave field is applied by the coaxial probe when supplied with radio frequency power from the power supply, the support having a flat support surface with an opening therein.

2. The apparatus of claim 1 further including a microwave detector coupled to the coaxial probe to receive a microwave signal reflected from the supported biochemical membrane.

3. The apparatus of claim 1 further including a receiving coaxial probe, having a core tip and a coaxial shield electrically insulated therefrom, forming a receiving probe for receiving microwaves, positioned closely adjacent to the biochemical membrane on the opposite side of the membrane from the coaxial probe to receive microwave power passed through the biological membrane, and a detector coupled to the receiving probe to detect the microwave signal received by the receiving probe.

4. The apparatus of claim 1 wherein the coaxial probe is connected to a resonant circuit and a feedback oscillator such that the frequency of the circuit changes with changes in the resonant frequency of the coaxial probe as capacitively coupled to the adjacent biochemical membrane.

5. The apparatus of claim 1 further comprising the biochemical membrane, wherein the biochemical membrane is a lipid bilayer.

6. The apparatus of claim 1 wherein the power supply provides output power in the range of at least 200 MHz.

7. Apparatus for high frequency interfacing to biochemical membranes comprising:

(a) a coaxial probe having an inner conductive core tip and a coaxial conductive shield electrically insulated from the core tip, wherein the core tip of the coaxial probe has a tip end diameter of 10 µm or less;

(b) a radio frequency power supply coupled to the coaxial probe to provide a radio frequency drive signal thereto; and (c) a support for a biochemical membrane positioned closely adjacent to the coaxial probe such that a localized microwave field is applied by the coaxial probe when supplied with radio frequency power from the power supply.

8. The apparatus of claim 1 wherein the power supply is coupled to the coaxial probe by a coaxial transmission line.

9. Apparatus for high frequency interfacing to biochemical membranes comprising:

(a) a coaxial probe having an inner conductive core tip and a coaxial conductive shield electrically insulated from the core tip;

(b) a radio frequency power supply coupled to the coaxial probe to provide a radio frequency drive signal thereto;

(c) a support for a biochemical membrane positioned closely adjacent to the coaxial probe such that a localized microwave field is applied by the coaxial probe when supplied with radio frequency power from the power supply; and (d) a scanning force microscope mounting system to which the coaxial probe is mounted for displacement by the scanning force microscope mounting system relative to a supported membrane in two dimensions.

10. Apparatus for high frequency interfacing to biochemical membranes comprising:

(a) a coaxial probe having an inner conductive core tip and a coaxial conductive shield electrically insulated from the core tip;

(b) a radio frequency power supply coupled to the coaxial probe to provide a radio frequency drive signal thereto; and (c) a support for a biochemical membrane positioned closely adjacent to the coaxial probe such that a localized microwave field is applied by the coaxial probe when supplied with radio frequency power from the power supply;

wherein there are multiple coaxial probes supported on a substrate and arranged in a two-dimensional array.

11. The apparatus of claim 10 including multiple fluid holding cells, with one of the coaxial probes underlying each of the cells.

12. The apparatus of claim 10 wherein the core tips of the coaxial probes are micromachined of silicon.

13. The apparatus of claim 10 wherein the coaxial probes are formed with the core tips of the coaxial probes electrically conductive and mounted in an array on a substrate, and including a support plate spaced from the substrate with openings therein adjacent to and with walls thereof closely spaced to the core tips, the walls of the openings in the support plate having a conductive material to form coaxial shields adjacent to the core tips.

14. Apparatus for high frequency interfacing to biochemical membranes comprising:

(a) a coaxial probe having an inner conductive core tip and a coaxial conductive shield electrically insulated from the core tip;

(b) a radio frequency power supply coupled to the coaxial probe to provide a radio frequency drive signal thereto;

(c) a support for a biochemical membrane positioned closely adjacent to the coaxial probe such that a localized microwave field is applied by the coaxial probe when supplied with radio frequency power from the power supply; and (d) chambers for containing fluid on each of two sides of the support for the biochemical membrane, and including electrodes inserted into the compartments to make contact with the fluid therein and connected to a power supply to provide an electrical potential between the electrodes across the membrane, and including a detector connected to the electrodes for detecting current flow between the electrodes.

15. A method for high frequency interfacing to biochemical membranes comprising:

(a) supporting a biochemical membrane having an exposed surface on a support, wherein the support includes a flat support surface with an opening therein, and further wherein the membrane spans the opening;

(b) positioning a coaxial probe adjacent to the membrane spanning the opening, the coaxial probe having an inner core tip and a coaxial shield around the core tip that is electrically insulated therefrom; and (c) supplying radio frequency power to the coaxial probe to apply a radio frequency field to the membrane adjacent to the coaxial probe.

16. The method of claim 15 further including detecting changes in the capacitive coupling of the radio frequency power provided to the membrane from the coaxial probe to detect fluctuations due to transport events across the biochemical membrane.

17. The method of claim 15 wherein the electromagnetic radiation reflected from the membrane received by the coaxial probe tip is detected.

18. The method of claim 15 further including positioning a receiving coaxial probe adjacent to and on the side of the membrane opposite to the coaxial probe and receiving electromagnetic power transmitted across the membrane to provide a signal and detecting the signal to determine fluctuations in the electromagnetic field transmitted across the membrane.

19. The method of claim 15 wherein the biochemical membrane comprises a lipid bilayer.

20. The method of claim 15 further including scanning the coaxial probe with respect to the exposed surface of the membrane in a selected pattern.

21. The method of claim 15 wherein in the step of supporting a biochemical membrane, the membrane is a cell membrane of a biological cell.

22. The method of claim 15 including coupling the electromagnetic power reflected from the membrane received by the coaxial probe to a resonant circuit with a feedback oscillator such that the frequency of oscillation varies with changes in the charge across the membrane.

23. The method of claim 15 including rectifying a component of the radio frequency field applied to the membrane to apply a DC potential across the membrane.

* * * * *